United States Patent [19]

Richardson et al.

[11] Patent Number: 5,146,930
[45] Date of Patent: Sep. 15, 1992

[54] CONTRACEPTIVE AND ANTI-INFECTIVE BARRIER DEVICE

[76] Inventors: Margaret P. Richardson; Philip Richardson, both of The Bungalow, Pibwrlwyd Lane, Carmarthen, United Kingdom

[21] Appl. No.: 794,803

[22] Filed: Nov. 8, 1991

Related U.S. Application Data

[63] Continuation of Ser. No. 569,514, Aug. 20, 1990, abandoned, which is a continuation of Ser. No. 391,583, Jul. 18, 1989, abandoned.

[30] Foreign Application Priority Data

Feb. 22, 1987 [WO] PCT Int'l Appl. ... PCT/GB88/00042
Feb. 11, 1987 [GB] United Kingdom ............ 8703157
Feb. 22, 1987 [GB] United Kingdom ............ 8701385

[51] Int. Cl.⁵ .................... A61F 6/06; A61F 6/04
[52] U.S. Cl. .............................. 128/830; 128/842
[58] Field of Search ............ 128/830, 834, 835, 838, 128/842, 844

[56] References Cited

U.S. PATENT DOCUMENTS

| | | | |
|---|---|---|---|
| 1,123,994 | 1/1915 | Cranston | 128/835 |
| 3,536,066 | 10/1970 | Ludwig | 128/844 |
| 3,709,220 | 1/1973 | Boyden | 128/132 |
| 4,664,104 | 5/1987 | Jaicks | 128/132 |
| 4,735,621 | 4/1988 | Hessel | 128/844 X |
| 4,798,600 | 1/1989 | Meadows | 128/844 X |
| 4,805,604 | 2/1989 | Spery | 128/830 X |
| 4,832,052 | 5/1989 | Mohajer | 128/834 X |
| 4,834,113 | 5/1989 | Reddy | 128/830 X |
| 4,867,176 | 9/1989 | Lash | 128/830 |

FOREIGN PATENT DOCUMENTS

210413 1/1908 Fed. Rep. of Germany.

Primary Examiner—Robert A. Hafer
Assistant Examiner—Kevin G. Rooney
Attorney, Agent, or Firm—Reising, Ethington, Barnard, Perry & Milton

[57] ABSTRACT

The device includes a continuous flexible pouch which is entirely surrounded by a flange member which acts as a shield to cover the periphery of the vaginal entrance. The pouch, which is preferably in the form of a loose collapsed sheath, is arranged to be introduced into the user's vagina so as to form a liquid barrier between the penis and vagina. Straps and ribbed protrusions are provided for securely maintaining the flange member in its operational position. Preferably, an applicator rod is also provided.

28 Claims, 4 Drawing Sheets

CONTRACEPTIVE AND ANTI-INFECTIVE BARRIER DEVICE

This application is a continuation of application Ser. No. 569,514, filed Aug. 20, 1990, now abandoned, which is a continuation of Ser. No. 391,583, filed Jul. 18, 1989 now abandoned.

The present invention is concerned with barrier devices for use in contraception and in preventing transmission of sexually transmitted diseases.

Many types of contraceptive devices are known. Among these are condoms, diaphragms and other intra-vaginal devices, intra-uterine devices, spermicidal films etc. Of these, the only device which provides a barrier against transfer of body fluids between sexual partners is the condom; the use of a condom therefore helps to prevent sexual transmission of diseases. Indeed the use of a condom is positively recommended as a prophylactic measure against, in particular, acquired immune deficiency syndrome (AIDS).

The condom does have a number of disadvantages, however. Among such disadvantages are that it can only be donned on an erect penis, and therefore only immediately before intercourse. This is found to be off-putting by many users and the attendant delays can sometimes lead to loss of erection by the male. Furthermore, the condom permits contact between vaginal mucous membranes and the penis at the entrance to the vagina, with consequent risk of disease transmission, and may become dislodged under certain circumstances during intercourse (e.g. on loss of erection or withdrawal of the penis) with consequent failure of the contraceptive and disease-preventing barrier.

We have therefore devised a barrier device which at least alleviates some of these disadvantages and provides an alternative means of contraception and prevention of sexual transmission of diseases.

According to the present invention, therefore, there is provided a barrier device, which comprises a continuous impermeable shield member shaped and dimensioned so that, in operational position, it covers the entrance of a user's vagina, the shield member having integral therewith a continuous, impermeable, flexible pouch arranged to receive a penis and be introduced into the vagina so as to form a liquid barrier between the penis and vagina; and means for securing the shield member in said operational position on the female user's body.

The barrier device according to the invention can provide a substantially complete barrier against genital skin contact, and therefore offers greater disease protection than the conventional condom. In addition, it provides a contraceptive and protective device under the control of the female partner (in contrast to the condom, which is, of course, under the control of the male).

The pouch is typically in the form of a loose, collapsed sheath broadly similar to conventional male condoms, and may be of a similar type of material. It is particularly preferred that the pouch and the shield member comprise a single, continuous unitary body. Preferably, the pouch portion is provided with a lubricated surface both internally and externally.

The shield member may be in the form of a flexible membrane surrounding the pouch. Such a membrane and its associated pouch may be secured in the operational position by means of straps which pass around the hips and between the buttocks to form a G-string type garment; alternatively, the membrane may be provided secured in the operational position in a pantie-like garment.

Such a garment can be donned by the female at any time prior to intercourse and may be worn under normal panties. The device according to the invention is therefore unobtrusive and easy to use; in some embodiments it may be disposable after use. In such a garment, the pouch may be protected by a removable layer of paper, plastics or the like, both inside and out, until ready for use, at which point the protective layers would be removed and the pouch introduced into the vagina either manually, by means of an applicator, or by the penis.

In a further embodiment of the invention, the shield member may be secured in the operational position by means of formations (such as ribbed protrusions) adapted to engage the user's vagina. In this embodiment, the pouch may be retained in a relatively more rigid receptacle until required, and introduced into the vagina using an applicator rod of a similar nature to those used conventionally for introduction of tampons into the vagina.

The present invention will now be further described with reference to the accompanying drawings, in which.

Figure 1:
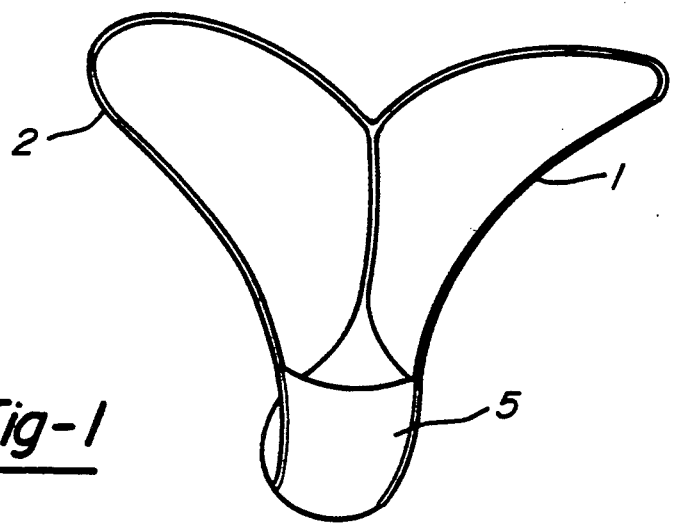
FIG. 1 is a schematic drawing showing a G-string type garment, which incorporates a membrane and pouch as described above to constitute a barrier device according to the invention (the pouch is not shown, for reasons of clarity)
Figure 2:
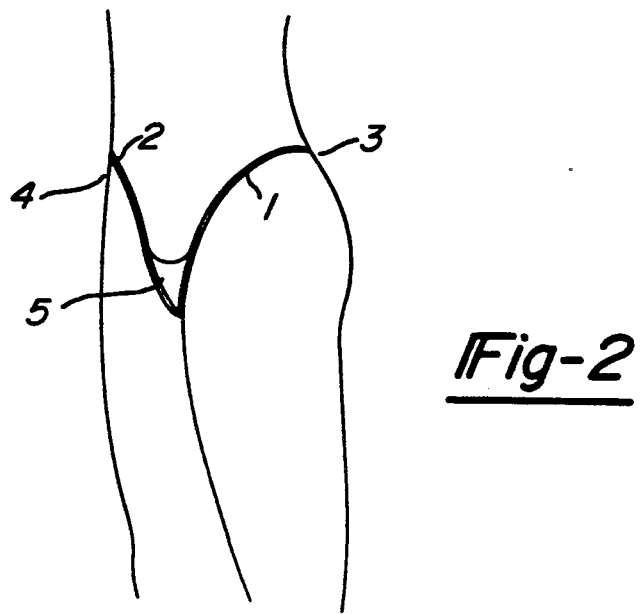
FIG. 2 is a schematic drawing showing the garment of FIG. 1 in its operational position.

Referring to FIGS. 1 and 2, there is shown a garment comprising a pair of straps 1,2 (typically elasticated), which pass around the hips 3,4 (FIG. 2) and retain a membrane 5 covering the vulva and therefore the vaginal entrance.

Figure 3:
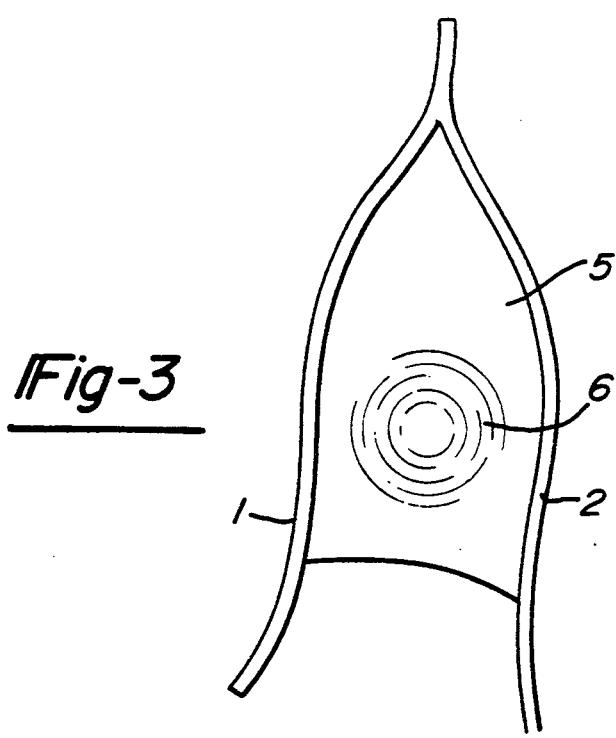
FIG. 3 shows in more detail the membrane and pouch as provided in the garment of FIG. 1.
Figure 4:
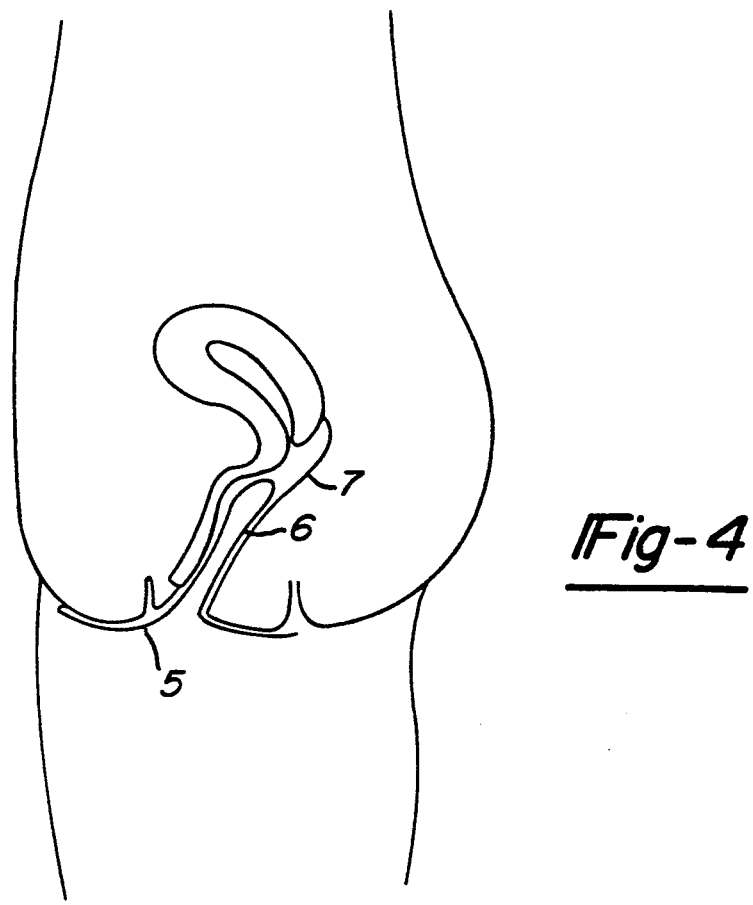
FIG. 4 shows the pouch in position in the vagina.

Referring to FIG. 3, the membrane 5 includes in a generally central location a collapsed pouch 6, which is arranged to be carried into and constitute a lining for the vagina 7 (as shown in FIG. 4).

Figure 5:
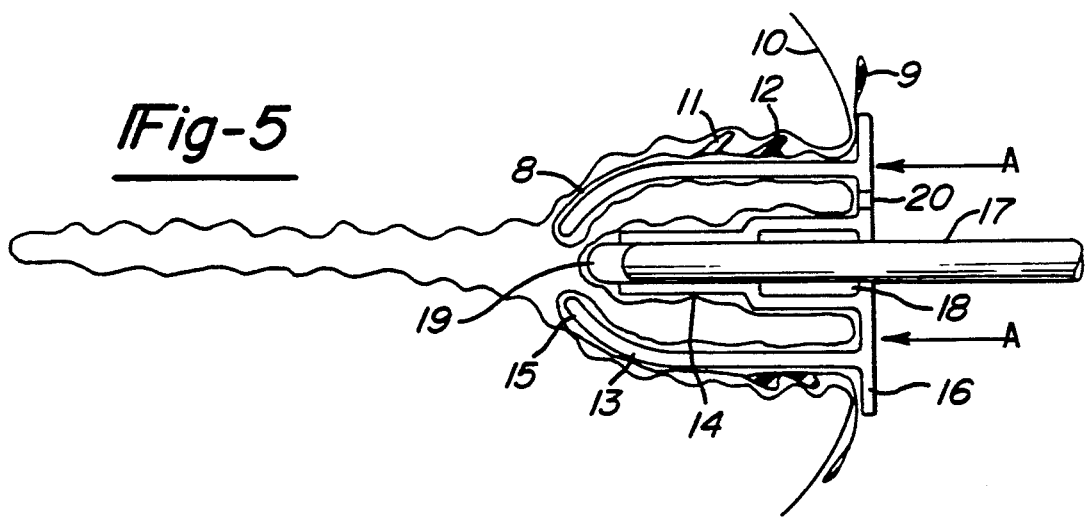
FIG. 5 is a schematic sectional drawing showing an exemplary barrier device according to the invention, present in an applicator (together with an applicator rod)

Referring to FIG. 5, there is shown a barrier device comprising a continuous flexible, liquid-impermeable pouch 8 which is entirely surrounded by a relatively more rigid flange member 9 which acts as a shield to cover the periphery of the vaginal entrance 10. Adjacent the flange member 9 are a series of flexible protrusions 11,12 which are inclined outwardly towards the vaginal entrance 10; the protrusions serve to retain the pouch in the operational position.

The pouch 8 is shown in convoluted form on a hollow, inwardly tapering applicator body 13; the applicator body has an inner wall 14 of generally cylindrical section and an outer wall 15 which smoothly and gently tapers inward.

The outer wall 15 has an outer peripheral flange 16 for engagement with the flange member 9 to prevent insertion of an applicator rod 17 too far into the vagina. The convolutions of the pouch 8 are such that the end portion thereof is retained within the applicator body until it is ready for use.

Figure 6:
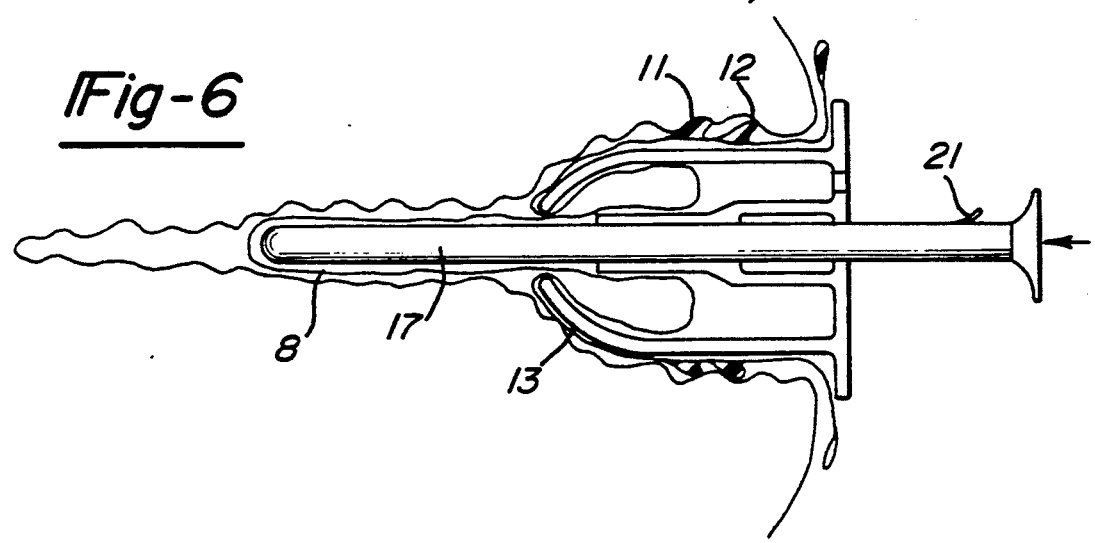
FIGS. 6 and 7 show the progressive introduction of the flexible pouch into the vagina using the applicator rod.
Figure 7:
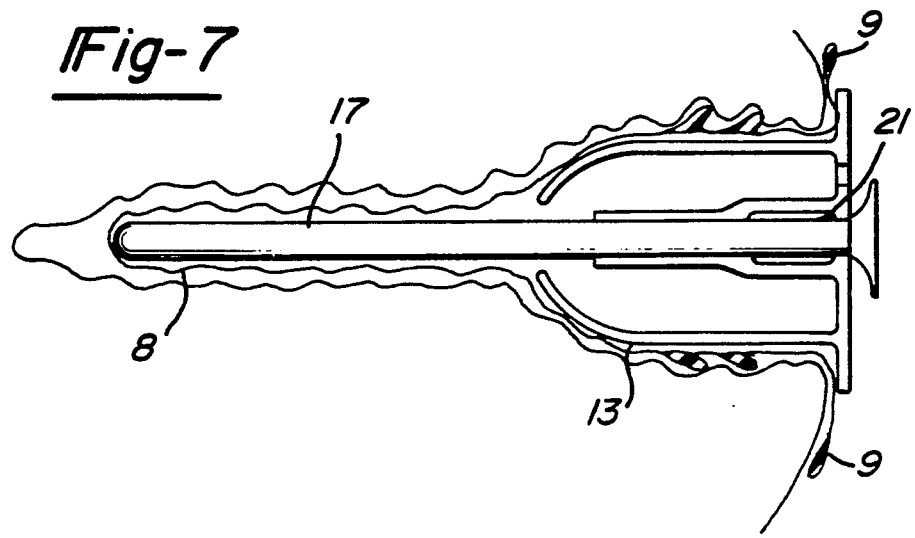

In use, the applicator body 13 is inserted in the vaginal entrance 10 immediately prior to coitus and the applicator rod 17 inserted through the hollow central portion 18 of the body 13, in the direction of arrows A. The applicator rod 17 breaks a lubricant capsule 19 so that lubricant material is distributed throughout the pouch. The applicator rod 17 is then pushed further into the vagina (FIG. 6) until the pouch is fully extended (FIG. 7) and flange 16 engages flange member 9; as this takes place, air communication is permitted to the interior of the applicator body 13 via aperture 20.

Figure 8:
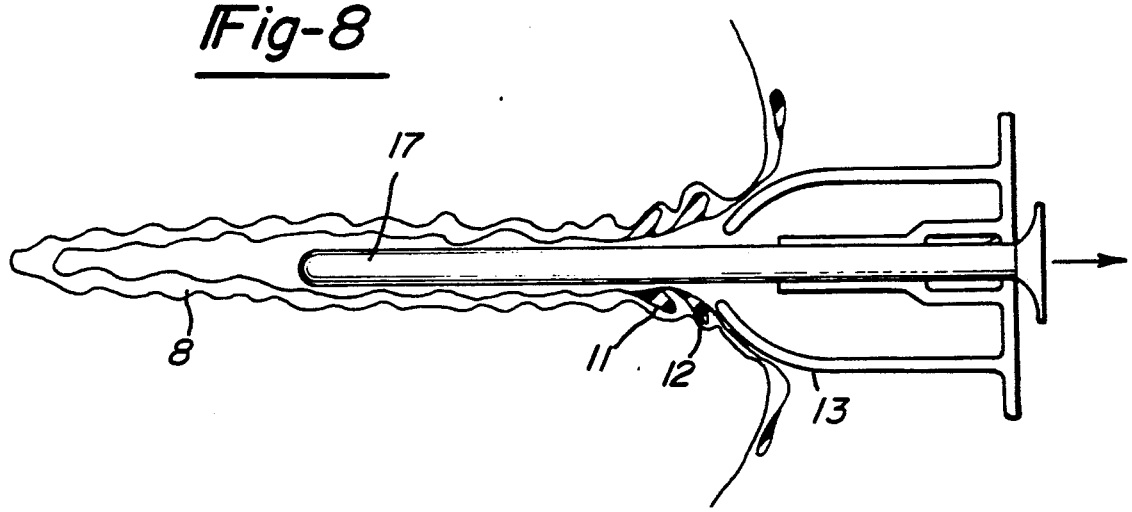
FIG. 8 shows the withdrawal of the applicator rod once the pouch has been fully introduced into the vagina.

As the pouch 8 is introduced into the vagina, the protrusions 11,12 engage the vaginal wall. As the applicator rod 17 is inserted to its full extent, a catch 21 engages the interior of the applicator body 13; the rod 17 and the applicator body 13 can then be removed by pulling outward leaving the pouch 8 installed in its operational position already lubricated on its internal surface (see FIG. 8).

Figure 9:
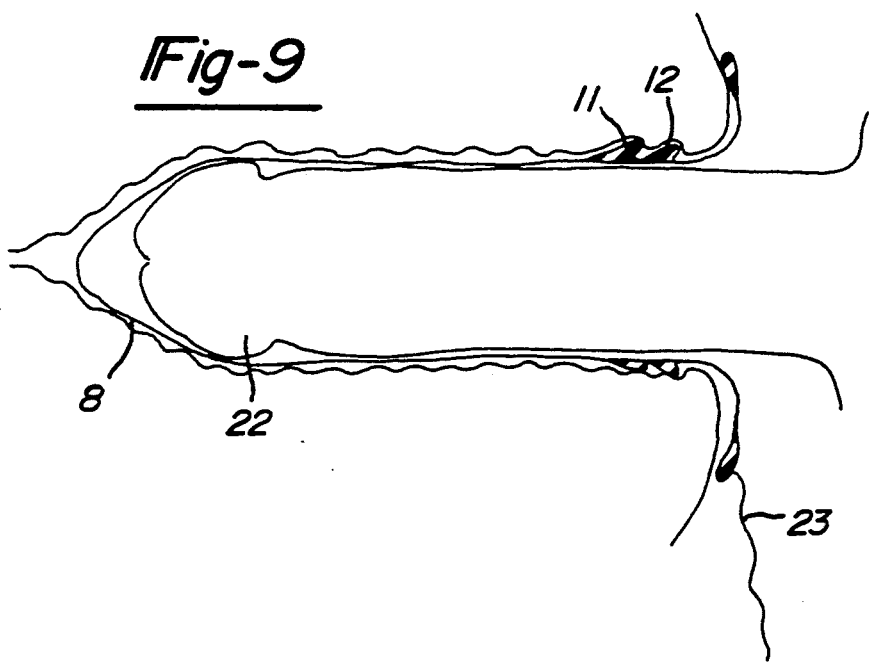
FIG. 9 shows how the pouch is retained in position in the vagina after entry of the penis of the user's partner.

Intercourse can then take place (see FIG. 9) by insertion of the penis 22, whereupon the protrusions 11, 12 serve to retain the pouch 8 in position, the latter acting as a sheath for the penis. The flange member 9 is arranged to prevent the pouch 8 entering too far into the vagina.

After intercourse, the pouch 8 can be removed from the vagina by pulling on a drawstring 23 attached to flange member 9. This is facilitated by protrusions 11, 12 disengaging from the vaginal folds as soon as pressure from the penis is removed.

In the embodiment of the invention as just described with reference to FIGS. 5 to 9 of the drawings, the pouch can be readily placed in the correct operational position by means of the shaped applicator; the insertion operation is already familiar to many women as it corresponds to the way in which tampons are conventionally inserted.

While the present invention has been described in terms of a device to be worn by a female, the present invention further comprises a modification of the device which is such that it can be worn by a male homosexual. In this modification of the device according to the invention, the pouch would be intended to be introduced into a male partners anal passage, and previous references herein to the vagina should be construed to refer to the anal passage in this modification of the invention.

We claim:

1. In combination, a contraceptive, anti-infective barrier device for use by a female user, and an applicator member therefor, in which the barrier device comprises: (a) a continuous, liquid impermeable flexible pouch having an open end and a closed end such that the pouch can be introduced into a user's vagina and subsequently receive a penis; (b) a continuous, liquid-impermeable peripheral flange integral with the open end of said pouch, the flange being shaped and dimensioned such that when said pouch has been introduced into the vagina, the flange covers the periphery of the vaginal entrance and said flange and said pouch together form a barrier to liquid passing between the penis and the vagina; (c) a peripheral rim surrounding said flange said rim and said flange not forming part of a garment to pass around the legs of the user; and (d) projecting formations provided on set pouch proximate said flange portion for engaging the internal walls of the vagina such that said flange is retained in the position in which it covers the periphery of the vaginal entrance and in which the applicator comprises an elongate body which is arranged to introduce said pouch into said vagina and be withdrawn therefrom leaving said pouch in place.

2. A combination according to claim 1, in which said pouch is in the form of a loose, collapsed sheath.

3. A combination according to claim 1, in which said pouch has a lubricated surface both internally and externally.

4. A combination according to claim 1, in which said means for engaging the walls of the vagina comprises formations adapted to engage the user's vaginal walls adjacent the vaginal entrance.

5. A combination according to claim 1, in which said pouch is provided with a removable covering layer of sheet material.

6. A combination according to claim 1, further comprising an applicator body comprising a tubular member having said pouch located therearound, with the closed end thereof within said tubular member.

7. A combination according to claim 6, wherein the outer surface of said applicator body tapers inwardly from the end of said tubular member adjacent the open end of said pouch.

8. A combination according to claim 6, in which said applicator body further comprises an inner tubular member shaped and dimensioned to slidably receive said applicator member.

9. In combination, a contraceptive anti-infective barrier device for use by a female user, and an inanimate applicator member therefor, in which the barrier device comprises: (a) a continuous, liquid-impermeable, flexible pouch having an open end and a closed end such that the pouch can be introduced into a user's vagina and subsequently receive a penis; (b) a continuous liquid-impermeable peripheral flange integral with the open end of said pouch, the flange being shaped and dimensioned such that when said pouch has been introduced into the vagina, the flange covers the periphery of the vaginal entrance and said flange and said pouch together forming a barrier to liquid passing between the penis and the vagina; (c) a peripheral rim surrounding said flange wherein neither said rim nor said flange form a part of a garment to pass around the legs of the user; and (d) projecting formations provided on said pouch proximate said flange for engaging the walls of the vagina such that said flange is retained in the position in which it covers the periphery of the vaginal entrance, wherein the applicator member is shaped and dimensioned for introduction of said pouch into said vagina and withdrawal therefrom leaving said pouch in place, said means being arranged to retain said pouch in position within the vagina when said applicator member has been withdrawn from said pouch with said pouch in place in said vagina.

10. A combination according to claim 9, in which said pouch is in the form of a loose, collapsed sheath.

11. A combination according to claim 9, in which said pouch is provided with a lubricated surface both internally and externally.

12. A combination to claim 9, in which said pouch is provided with a removable covering layer of sheet material.

13. A combination according to claim 9, further comprising an applicator body comprising a tubular member having said pouch located therearound with the closed end thereof within said tubular member.

14. A combination according to claim 13, wherein said applicator body includes an outer surface tapering inwardly from the end of said tubular member adjacent the open end of said pouch.

15. A combination according to claim 13, in which said applicator body further comprises an inner tubular member shaped and dimensioned to slideably receive said applicator member.

16. In combination, a contraceptive, anti-infective barrier device for use by a female user, and an applicator member therefor, in which the barrier device comprises: (a) a continuous, liquid-impermeable, flexible pouch having an open end and a closed end such that the pouch can be introduced into a user's vagina and subsequently receive a penis; (b) a continuous, liquid-impermeable, peripheral flange being shaped and dimensioned such that when said pouch has been introduced into the vagina, the flange covers the periphery of the vaginal entrance and said flange and said pouch together form a barrier to liquid passing between the penis and vagina; (c) a peripheral rim around said flange wherein neither said rim nor said flange forms part of a garment to pass around the legs of said user; and (d) projecting formations provided on said pouch for engaging the internal walls of the vaginal adjacent the vaginal entrance such that said flange is retained in the position in which it covers the periphery of the vagina entrance; and in which the applicator member is arranged to introduce said pouch into said vagina and be withdrawn therefrom leaving said pouch in place.

17. A combination according to claim 16, in which said pouch is in the form of a loose, collapsed sheath.

18. A combination according to claim 16, in which said pouch is provided with a lubricated surface both internally and externally.

19. A combination according to claim 16, in which said pouch is provided with a removable covering layer of sheet material.

20. A combination according to claim 16, further comprising an applicator body comprising a tubular member having said pouch located therearound, with the closed end thereof within said tubular member.

21. A combination according to claim 20, wherein the outer surface of said applicator body tapers inwardly from the end of said tubular member adjacent the open end of said pouch.

22. A combination according to claim 20, in which said applicator body further comprises an inner tubular member shaped and dimensioned to slideably receive said applicator member.

23. A method of inserting a contraceptive, anti-infective barrier device into the vagina of a female user, which comprises; (a) providing a barrier device comprising a continuous, liquid-impermeable, flexible pouch having an open end and a closed end; a continuous, liquid-impermeable peripheral flange integral with the open end of said pouch; a peripheral rim surrounding said flange wherein said rim and flange do not form part of a garment to pass around the legs of the user; and projecting formations provided on said pouch proximate said flange portion for engaging the internal walls of said vagina; (b) inserting said pouch into said vagina by means of an applicator member such that said flange covers the periphery of the entrance to said vagina; and (c) withdrawing said applicator member prior to coitus so as to leave pouch in place in said vagina so as to be capable of receiving a penis therein.

24. A method according to claim 23, wherein said pouch is provided with a lubricated surface both internally and externally.

25. In combination, a contraceptive, anti-infective barrier device for use by a female user, and an applicator member therefor, in which the barrier device comprises: (a) a continuous, liquid-impermeable, flexible pouch having an open end and a closed end such that the pouch can be introduced into a user's vagina and subsequently receive a penis; (b) a continuous, liquid-impermeable peripheral flange being shaped and dimensioned such that when said pouch has been introduced into the vagina, the flange covers the periphery of the vaginal entrance and said flange and said pouch together form a barrier to liquid passing between the penis and the vagina; (c) a peripheral rim surrounding said flange, wherein said rim and/or said flange do not form part of a garment to pass around the legs of said user; and (d) projecting formations provided on said pouch for engaging the internal walls of the vagina adjacent the vaginal entrance such that said flange is retained in the position in which it covers the periphery of the vaginal entrance; and in which the applicator member is arranged to introduce said pouch into said vagina and be withdrawn therefrom leaving said pouch in place.

26. In combination, a contraceptive, anti-infective barrier device for use by a female user, and an applicator member therefor, in which the barrier device comprises: (a) a continuous, liquid-impermeable, flexible pouch having an open end and a closed end such that the pouch can be introduced into a user's vagina and subsequently receive a penis; (b) a continuous, liquid-impermeable peripheral flange being shaped and dimensioned such that when said pouch has been introduced into the vagina, the flange covers the periphery of the vaginal entrance and said flange and said pouch together form a barrier to liquid passing between the penis and vagina; (c) a peripheral rim surrounding said flange wherein neither said rim nor said flange forms part of a garment to pass around the legs of said user; and (d) projecting formations provided on said pouch for engaging the internal walls of the vagina adjacent the vaginal entrance such that said flange is retained in the position in which it covers the periphery of the vaginal entrance; and in which the applicator member is arranged to introduce said pouch into said vagina and be withdrawn therefrom leaving said pouch in place, said projecting formations being the sole means for retaining the flange in place covering said periphery of said vagina.

27. An anti-infective barrier device for protection against sexually transmitted diseases, which comprises: (a) a continuous, liquid impermeable, flexible pouch having an open end and a closed end such that the pouch can be introduced into a user's sexual passage and subsequently receive a penis; (b) a continuous liquid-impermeable peripheral flange portion integral with the open end of said pouch, the flange being shaped and dimensioned such that when said pouch has been introduced into said passage, said flange portion covers the periphery of the entrance to said passage, wherein said flange portion and said pouch together form a barrier to liquid passing between said penis and said passage; (c) a peripheral rim surrounding said flange, said rim and said flange not forming part of a garment to pass around the legs of the user; and (d) projecting formations provided on said pouch proximate said flange portion for retaining said flange in the portion in which said flange portion covers the periphery of said entrance.

28. An anti-infective barrier device for protection against sexually transmitted diseases, which comprises: (a) a continuous, liquid impermeable, flexible pouch having an open end and a closed end such that the pouch can be introduced into a user's vagina and subsequently receive a penis; (b) a continuous liquid-impermeable peripheral flange portion integral with the open end of said pouch, the flange being shaped and dimensioned such that when said pouch has been introduced into said passage, said flange portion covers the periphery of the entrance to said passage, wherein said flange portion and said pouch together form a barrier to liquid passing between said penis and said passage; (c) a peripheral rim surrounding said flange, said rim and said flange not forming part of a garment to pass around the legs of the user; and (d) projecting formations provided on said pouch proximate said flange portion for engaging the internal walls of the vagina adjacent the vaginal entrance such that said flange is retained in the position in which said flange portion covers the periphery of said entrance.

* * * * *